(12) United States Patent
Barker et al.

(10) Patent No.: US 7,078,697 B2
(45) Date of Patent: Jul. 18, 2006

(54) THERMALLY POWERED TERAHERTZ RADIATION SOURCE USING PHOTONIC CRYSTALS

(75) Inventors: Delmar L. Barker, Tucson, AZ (US); William R. Owens, Tucson, AZ (US); Ross D. Rosenwald, Tucson, AZ (US); Nitesh N. Shah, Tucson, AZ (US); Hao Xin, Tucson, AZ (US)

(73) Assignee: Raytheon Company, Waltham, MA (US)

( * ) Notice: Subject to any disclaimer, the term of this patent is extended or adjusted under 35 U.S.C. 154(b) by 132 days.

(21) Appl. No.: 10/960,679

(22) Filed: Oct. 7, 2004

(65) Prior Publication Data

US 2006/0076518 A1 Apr. 13, 2006

(51) Int. Cl.
*G01N 21/61* (2006.01)
*H01J 25/00* (2006.01)

(52) U.S. Cl. .................. 250/343; 250/492.3; 250/493; 315/505

(58) Field of Classification Search ............... 250/504, 250/493, 368, 362, 343, 342; 359/573, 576; 385/123, 125
See application file for complete search history.

(56) References Cited

U.S. PATENT DOCUMENTS

| | | | |
|---|---|---|---|
| 6,002,522 A * | 12/1999 | Todori et al. ............... 359/573 |
| 6,144,679 A * | 11/2000 | Herman et al. ............... 372/21 |
| 6,618,535 B1* | 9/2003 | Reynolds ..................... 385/129 |
| 6,690,023 B1* | 2/2004 | Silivra ....................... 250/492.3 |
| 6,753,662 B1* | 6/2004 | Krafft .......................... 315/505 |
| 6,756,594 B1* | 6/2004 | George et al. ............. 250/343 |
| 6,893,502 B1* | 5/2005 | Papadimitrakopoulos et al. .............................. 117/92 |
| 2003/0219052 A1* | 11/2003 | Goodhue et al. ............. 372/45 |
| 2004/0013377 A1* | 1/2004 | Han ........................... 385/125 |
| 2004/0075464 A1* | 4/2004 | Samuelson et al. .......... 326/37 |
| 2004/0113103 A1* | 6/2004 | Zhilkov ................... 250/504 R |
| 2005/0121629 A1* | 6/2005 | Unterrainer et al. .... 250/504 R |
| 2005/0206020 A1* | 9/2005 | Baek et al. ................ 264/1.21 |
| 2005/0263269 A1* | 12/2005 | Kaneko et al. ............. 165/146 |

* cited by examiner

*Primary Examiner*—Kiet T. Nguyen
*Assistant Examiner*—Johnnie L. Smith, II
(74) *Attorney, Agent, or Firm*—Thomas J. Finn, Esq.; John E. Gunther; Karl A. Vick, Esq.

(57) ABSTRACT

Although THz radiation is naturally emitted by hot objects, the intensity levels are too weak to be considered as a practical THz source for most applications. Photonic crystal structures are used to modify the thermal emission peak associated with the standard Planck blackbody spectral distribution so that the THz region is dramatically enhanced. The photonic crystal core is preferably combined with variable Q defect cavities and a wave guiding and power combining structure so that the radiated THz energy is efficiently collected and directed to an output antenna. Higher THz emissions are realized by embedding a finer (higher frequency) photonic crystal structure within a coarser (lower frequency) structure.

25 Claims, 5 Drawing Sheets

THERMALLY POWERED TERAHERTZ RADIATION SOURCE USING PHOTONIC CRYSTALS

BACKGROUND OF THE INVENTION

1. Field of the Invention

This invention relates to thermally powered terahertz (THz) radiation sources and more specifically to the use of photonic crystals to shift the thermal emission peak associated with the standard Planck blackbody spectral distribution from the infrared (IR) band to the THz region.

2. Description of the Related Art

THz-frequency radiation, in the frequency region from 300 GHz to 10 THz, has been relatively unexploited compared to the adjacent radio frequency (RF) and IR spectral bands. This is largely because of transmission difficulties due to absorption by atmospheric water vapor but also due to a lack of practical radiation sources. In recent years there has been a significant growth of interest in applications of this previously underutilized portion of the electromagnetic spectrum. These applications include active short range imaging systems for concealed weapon detection or driving aids in dust or sand storms. The shorter wavelengths provide higher image resolution than is possible with traditional radar systems operating at radio frequencies. At longer ranges, the THz band is very useful for wide bandwidth space-based communications, high-resolution imaging of rotating satellites from another space-based platform and other space object surveillance applications. The lack of atmospheric attenuation at high altitudes permits use of THz radiation.

Spectroscopy is another application area for THz radiation. Many biological agents have abundant and easily recognized resonances in the THz region. From simple content analysis (material identification by exciting, then detecting molecular vibrational and rotation states) to spectroscopic imaging of trace clouds of biological agents, the THz spectrum promises to open many applications in the bio-detection area. Mounting a THz system on an unmanned aerial vehicle may make it possible to detect and map biological and certain chemical warfare agents on a battlefield. Researchers in the U.K. recently reported that THz radiation is 100% successful in detecting skin cancer, but they don't yet understand how (Scott, W. B., *Potential applications of terahertz signals spur scientists to explore RF/light border region*, Aviation Week & Space Technology, Jun. 21, 2004, page 68). Passive THz systems have also been used in astronomy to map molecular clouds in the galaxy.

One of the major bottlenecks for the successful implementation of THz-frequency systems is the limited output power of conventional THz sources. Most systems produce THz radiation via optical techniques, but those require massive lasers, complex optical networks and cooling systems. Some of the THz sources reported in the literature include optically pumped THz lasers, time-domain spectroscopy, backward wave oscillators, solid-state amplifiers combined with direct multipliers, and photo-mixers (Iida, M. et al., *Enhanced generation of terahertz radiation using 3D photonic crystals with a planar defect*, Proc. CLEO/QELS, June 2002 (Baltimore), Section CM1; Unterrainer, K. et al.; *Cavity enhanced few cycle THz generation and coherent spectroscopy*, Proc. CLEO/QELS, June 2002 (Baltimore), Section CM1; Han, H., Park, H., Cho, M., and Kim, J., *Terahertz pulse propagation in a plastic photonic crystal fiber*, Applied Physics Lett., 80 #15, 15 April 2002). The different sources have disadvantages including limited output power; excessive cost, size and weight; poor reliability and limited frequency agility.

SUMMARY OF THE INVENTION

The present invention provides a compact, reliable and low-cost THz source. This is accomplished with a thermally powered photonic crystal (PC) structure that generates a sharp emission peak in the THz region of a photonic crystal modified Planck spectrum. The photonic crystal is designed to shift the photon density of states (DOS) such that the thermal radiation from the broad IR Planck peak shifts to a sharp peak in the THz region (0.3–10 THz).

In one embodiment, the PC core is combined with a waveguide and power combining structure so that the radiated THz energy is efficiently collected and directed to an output antenna. More specifically, a plurality of defect cavities can be formed in the PC layer to collect and concentrate the radiation. The defect cavities then couple the radiation to an adjacent waveguide that directs the radiation to the output antenna.

In another embodiment, the PC core has two distinct photonic crystals, one that generates an emission peak near the desired THz region and one that creates a band gap outside the THz region. The additional band gap may be used to suppress thermal emission in the IR region of the Planck spectrum. The compounded response is accomplished by embedding a fine PC structure within a coarse PC structure. The multiply-embedded photonic crystal device provides additional degrees of freedom for designing the photon DOS in the core. Two or more embedded structures may be used depending on the range of radiation shift required. This concept can be applied to the wavelengths on either side of the THz region.

These and other features and advantages of the invention will be apparent to those skilled in the art from the following detailed description of preferred embodiments, taken together with the accompanying drawings, in which:

DETAILED DESCRIPTION OF THE INVENTION

The present invention describes how to control Planck radiation using photonic crystals (PCs) to create a new type of THz radiation source. A PC structure contains a periodic high-contrast modulation of the local index of refraction (or dielectric constant, for non-magnetic materials) in one, two or three dimensions (see for example J. D. Joannopoulos, R. D. Meade, and J. N. Winn, "Photonic Crystals: Molding the Flow of Light," Princeton: Princeton University Press (1995), or C. Lopéz, "Materials Aspects of Photonic Crystals," Advanced Materials 15, 1679 (2003)). Any two substances having sufficient contrast between their respective indices of refraction can be placed in a stable periodic arrangement with a particular geometry, spacing and shapes of the constituent substances to create a photonic crystal for a particular range of photon wavelengths. Radiation propagating in such a structure will undergo multiple Bragg scattering from the lattice array and multiple Mie scattering off the individual scattering elements. Under certain conditions, the multiply-scattered waves interfere destructively, resulting in minimal transmission over a broad range of wavelengths, which is termed the "band gap" (a term borrowed from semiconductor physics). The photonic band gap (PBG) is said to be complete when transmission is blocked for all angles of incidence and all polarization states within the wavelength band.

Figure 1:
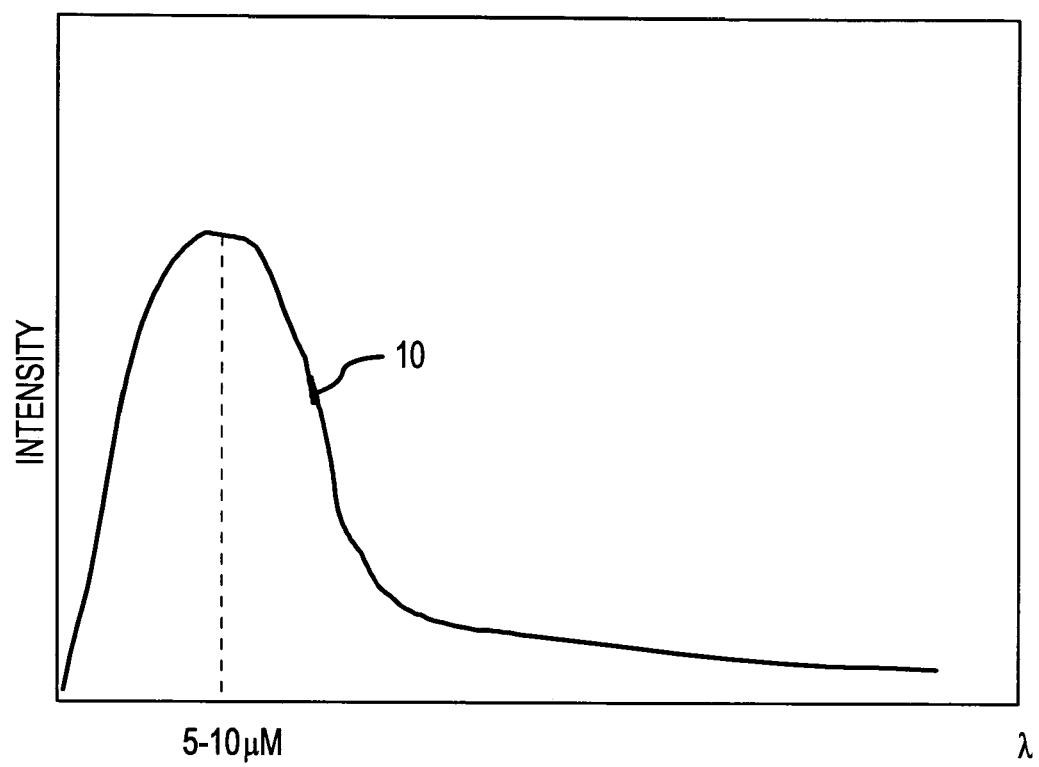
FIG. 1 is a plot of a normal Planck spectrum from a thermal blackbody radiator.

The new THz radiation source is powered by thermal energy associated with the heat capacity and temperature of the PC. It is well known that an object's Planck blackbody radiation spectrum 10 as shown in FIG. 1 may be strongly modified when the object is a photonic crystal with a band gap positioned around the peak (e.g., 5–10 µm) of the Planck spectrum. Several theoretical and experimental papers in this area have been published with very interesting results including Zhi-Yuan Li, Phys. Rev. B 66, R241103 (2002) and S-Y. Lin, et al, Phys. Rev. B 62, R2243 (2000), which are hereby incorporated by reference. Li models the redistribution of the photon density of states (DOS) in the emission region of the Planck spectrum as full and partial photonic band gaps that are manipulated by varying the crystal geometry and material. The conclusion is that a three-dimensional PC can induce strong redistribution of the photon DOS among different frequency bands. This redistribution can be used to modify thermal radiation from a blackbody when the PC is the blackbody.

In a designed PC as described in Li supra, orders-of-magnitude enhancement of the DOS can occur in low-DOS bands of the long-wavelength region. This leads to significantly enhanced thermal radiation emissions in the visible waveband (approximately 0.5 µm) for a modest cavity temperature. Since the underlying physics of the above conclusion should be generic, the physics can be applied to the thermally generated THz region of the spectrum as well (opposite frequency direction as compared to that discussed in Li supra).

The design and construction of photonic crystals with peaks and band gaps in the spectral regions of interest is existing art, for example, Lin supra. Waveguide channels and resonant cavities within photonic crystals are also well known art (see S. Noda et al., Science Vol. 239, p. 604, 28 Jul. 2000). The uniqueness of the present invention is to use and expand upon this knowledge to create a device that shifts thermal energy in the photonic crystal structure from the infrared spectral region towards the Terahertz spectral region and collects the internal energy for emission in a single direction.

Photonic Crystal THz Radiation Source

Figure 2:
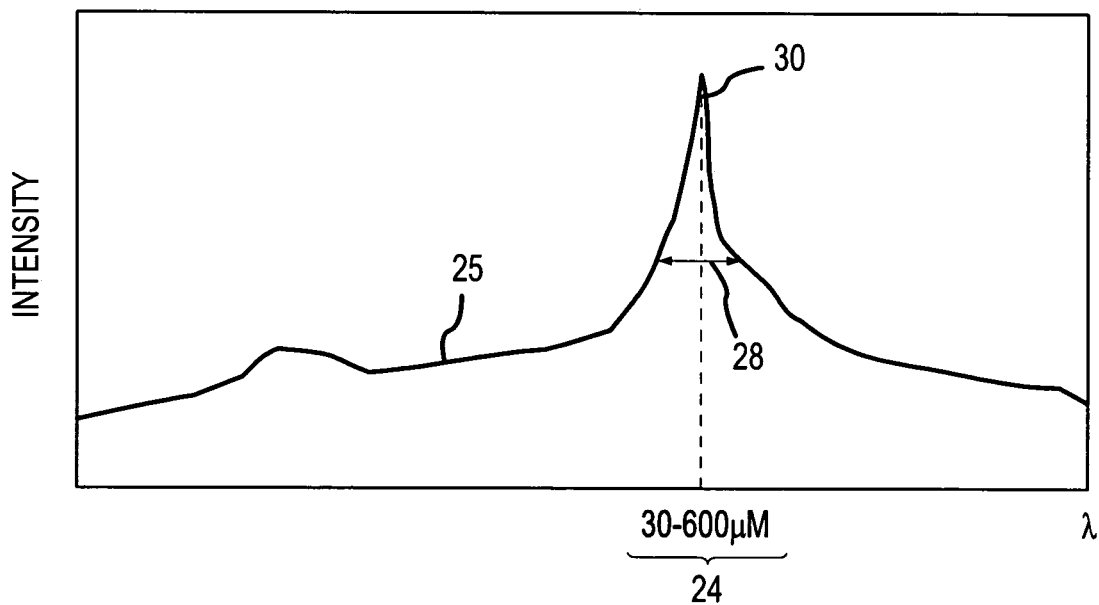
FIG. 2 is a plot of a photonic crystal modified Planck spectrum having a sharp emission peak in the THz region.
Figure 3:
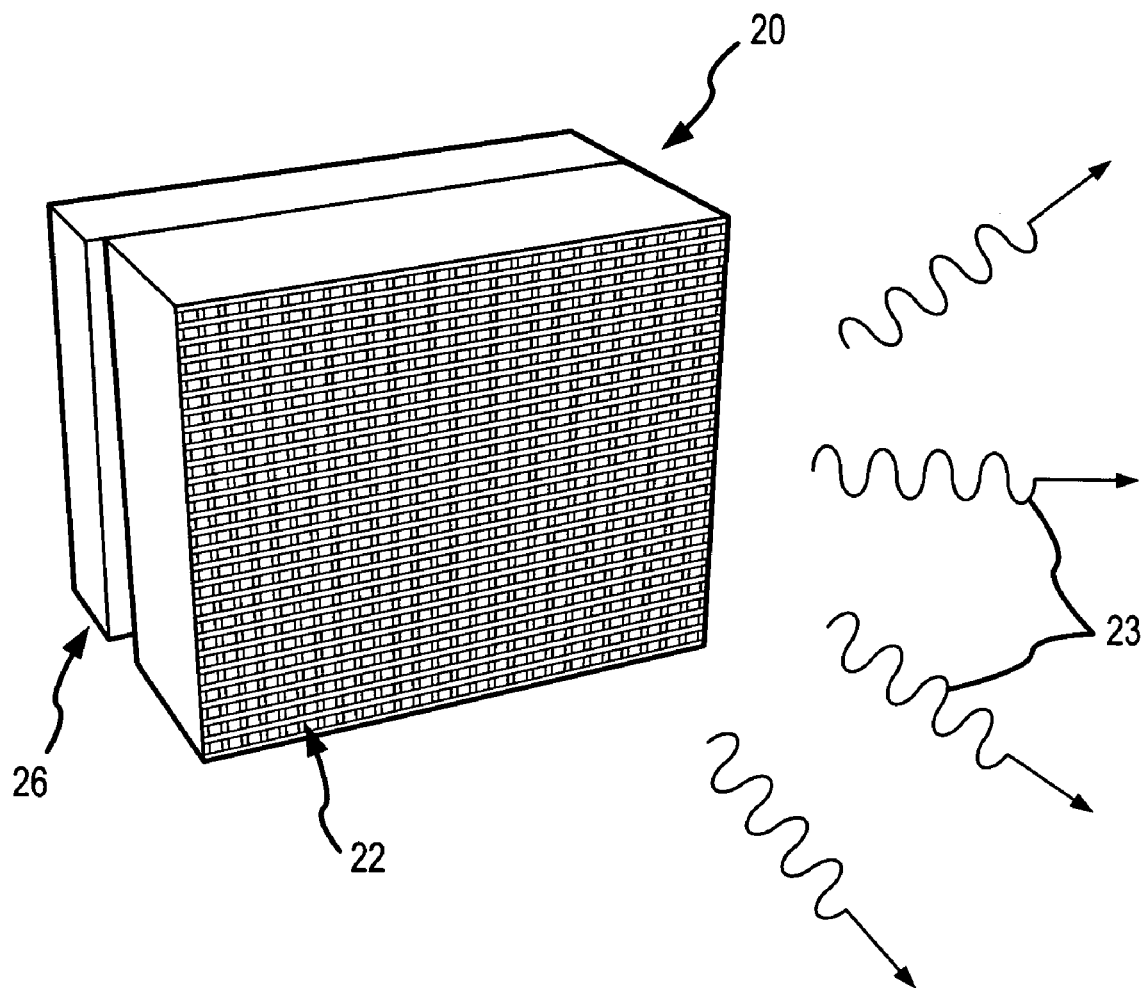
FIG. 3 is a perspective view of a thermally powered THz radiation source with a photonic crystal in accordance with the present invention.

As shown in FIGS. 2 and 3, in a PC-based THz radiation source 20 the DOS of a PC 22 is designed to dramatically enhance the spectral emissions 23 in the THz region 24 (0.3 THz to 10 THz), particularly when heated by a thermal source 26. The procedure utilized by Lin to directly engineer a nearby band gap is not effective in the thermally generated THz region because of the substantial wavelength separation between the initial and final wavelengths. The key point of the PC-based THz radiation source is the existence of peaks in its photon DOS. Using known design principles, a PC can be designed from computer simulation codes to have its DOS peak amplified dramatically in the desired THz band and suppressed elsewhere. Therefore, for any electromagnetic processes where thermal radiation is involved, the final emission states are constrained to the desired THz band by the use of a PC whose symmetries and lattice constants are distorted relative to a PC that has a strong PBG. Details about PC construction and properties can be found in Joannopoulos et al. supra and Lopéz supra, which are hereby incorporated by reference, among others.

As shown in FIGS. 2 and 3, the simplest structure is a single PC structure 22 in which the DOS is designed and optimized to create a modified Planck spectrum 25 in which the strongest possible emission peak is shifted toward the THz spectrum 24 by suitably at least a factor of 3. The bandwidth 28 of the emission peak 30 is less than 20% of the center frequency of the peak and preferably less than 10%, narrow enough to be useful in many imaging and spectroscopy applications. The thermal source 26 controls the temperature of the PC 22 from just above ambient temperature to just below the melting point of the crystal material such that increased output power is produced as needed. Temperatures range from 200 K to 2000 K but temperatures from 300 K to 1000 K are more typical based on the cost and reliability of the thermal source.

Waveguide and Power Combining Structure

Figure 4:
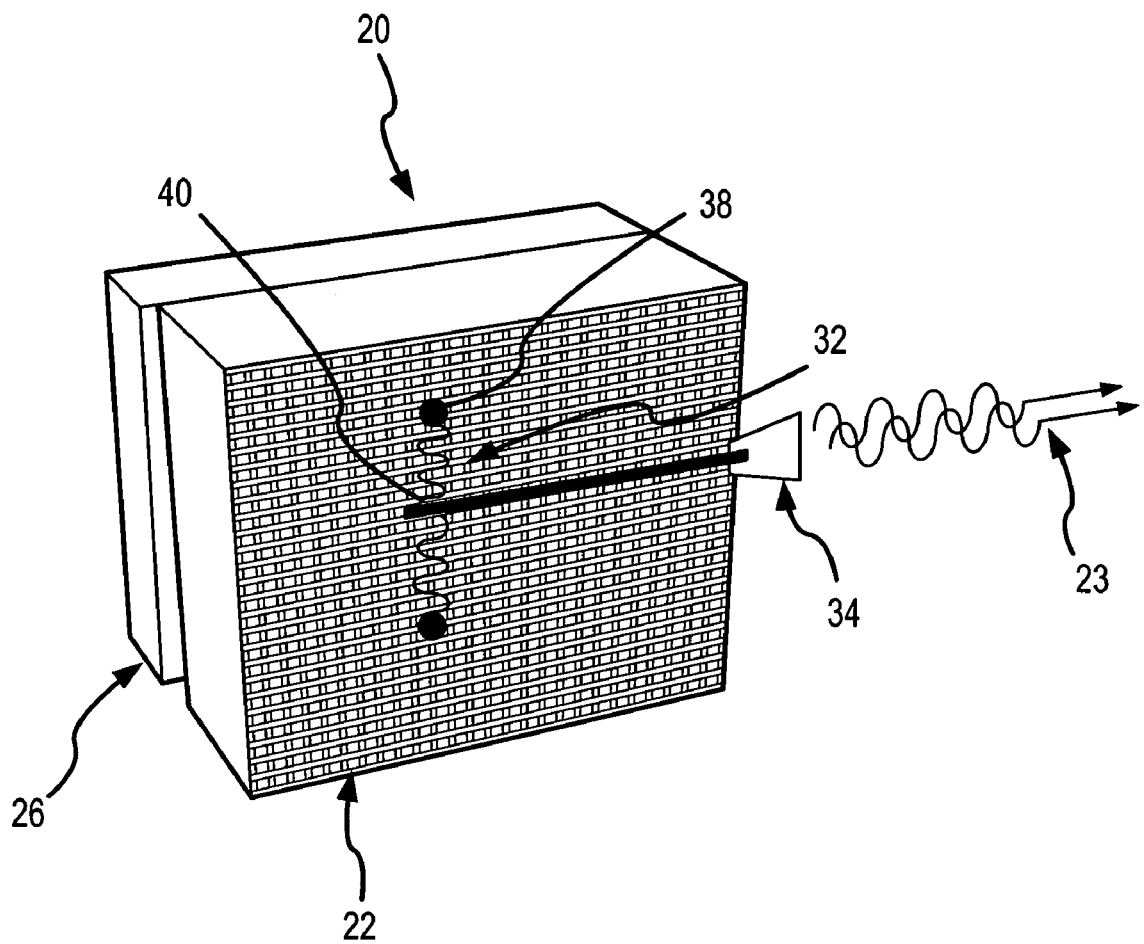
FIG. 4 is a perspective view of a radiation source having defect cavities and a waveguide structure within the photonic crystal core for guiding the THz radiation to an antenna.

As shown in FIG. 4, the PC core 22 (and thermal source 26) is combined with a wave guiding and power combining structure 32 so that the radiated THz energy is efficiently collected and directed to an output antenna 34. More specifically, a plurality of variable-Q defect cavities 38 collect and concentrate the radiation 23 in a limited bandwidth. The defect cavities then couple the radiation to a waveguide 40 that directs the radiation to the output antenna 34.

PCs possessing waveguides and defect cavities have been developed for fiber optical and millimeter wave applications. Recently, single mode PC waveguides (A. Scherer et al., IEEE Trans. Nanotech. 1, 4 (2002)), optical waveguides with sharp bends (A. Mekis et al., Phys. Rev. Lett. 77, 3787 (1996)), very high-Q cavity resonator (Y. Akahane et al., Nature 425, 944–947 (2003)), and PC with tunable band gap (H. Xin et al., IEEE Antennas and Propagation Symp. 2, 435 (2003)) have been demonstrated. They offer higher efficiency, smaller size and other unique advantages compared to conventional wave guiding components.

The wave guiding and power combining structure extracts energy from within the crystal into a combining network of waveguides with a consolidated output orifice. Rather than injecting external signals into the PC, the structure collects internal Planck radiation from the PC material. Defect cavities near the waveguides collect and concentrate a narrow spectral band of the radiation determined by the Q of the cavity.

In this embodiment, the plurality of defect cavities 38 is formed in the PC 22 to collect and concentrate the radiation 23. The defect cavities couple the radiation to the waveguide 40 formed in the PC 22 adjacent to the defect cavities to direct the radiation to a single narrow beam output antenna 34, which then emits the THz radiation 23. The defect cavities also act as narrowband resonators that generate the very narrow emission band 28 shown in FIG. 2. The defect cavities and waveguide are suitably voids in the PC structure. Various geometries and architectures can be designed and evaluated to achieve optimum results for a given wavelength and power. For example, the defect cavities 38 may be formed in a PC layer within the radiation core, which is designed to have a PBG in the desired THz band to achieve optimal coupling efficiency from the radiation core to the output antenna. The waveguide 40 is formed in the PC layer around the defect cavities to direct the radiation to the antenna. The design of the defect cavities depends on the application and the desired bandwidth.

THz Source with Embedded Photonic Crystal Structures

Figure 5:
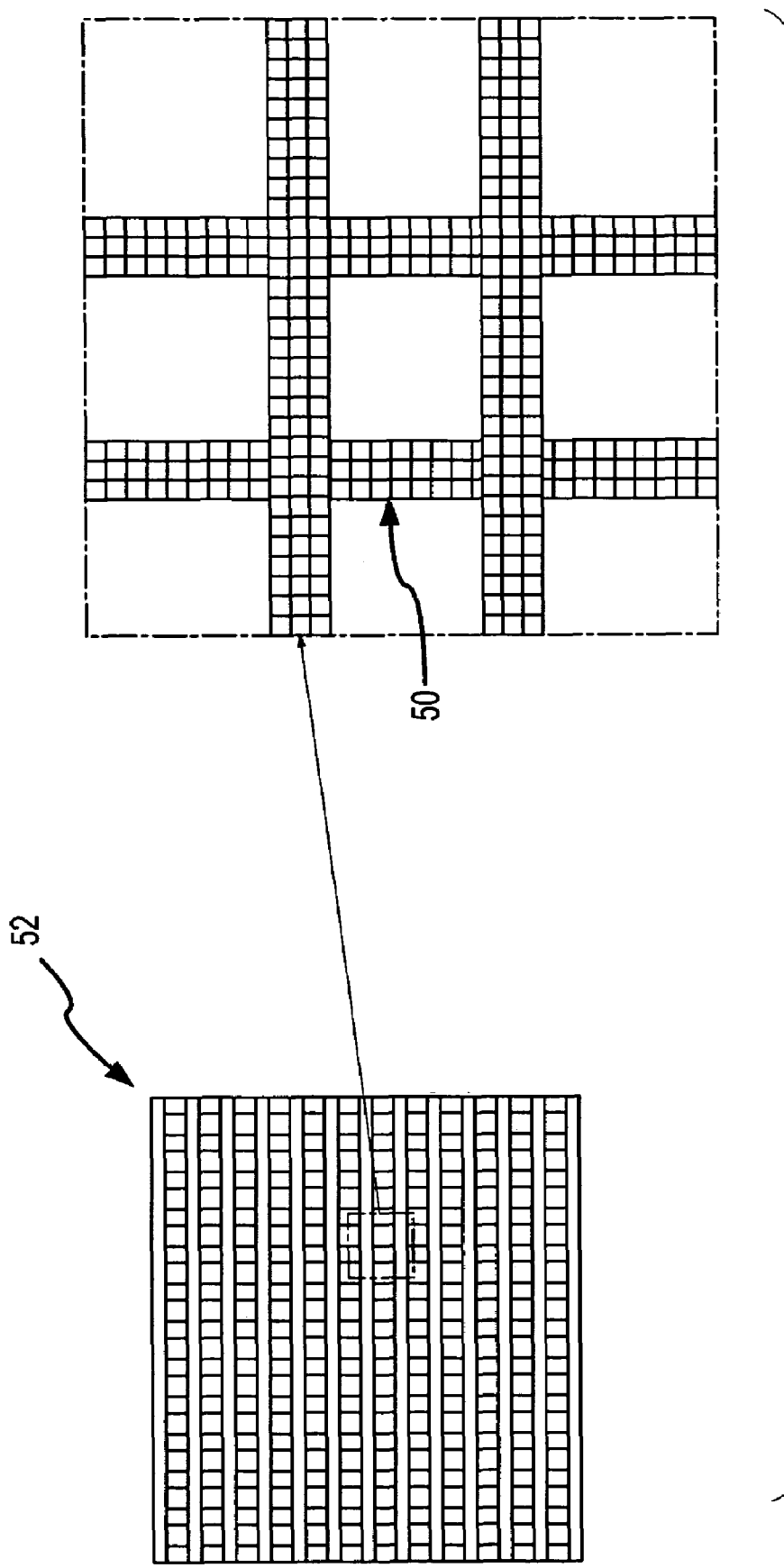
FIG. 5 illustrates a THz radiation source using embedded photonic crystal substructures.

In another embodiment, the PC core has two or more distinct PC structures, one with an emission peak near the desired THz region for wave guiding purposes and the other having a band gap at an independent frequency higher than THz. Since the unit-cell sizes of the PC structures giving rise to the two DOS distributions should be considerably different, the fine (higher frequency band) PC structure 50 can be embedded within the coarse (lower frequency band, e.g., THz) PC structure 52 as shown in FIG. 5.

Figure 6:
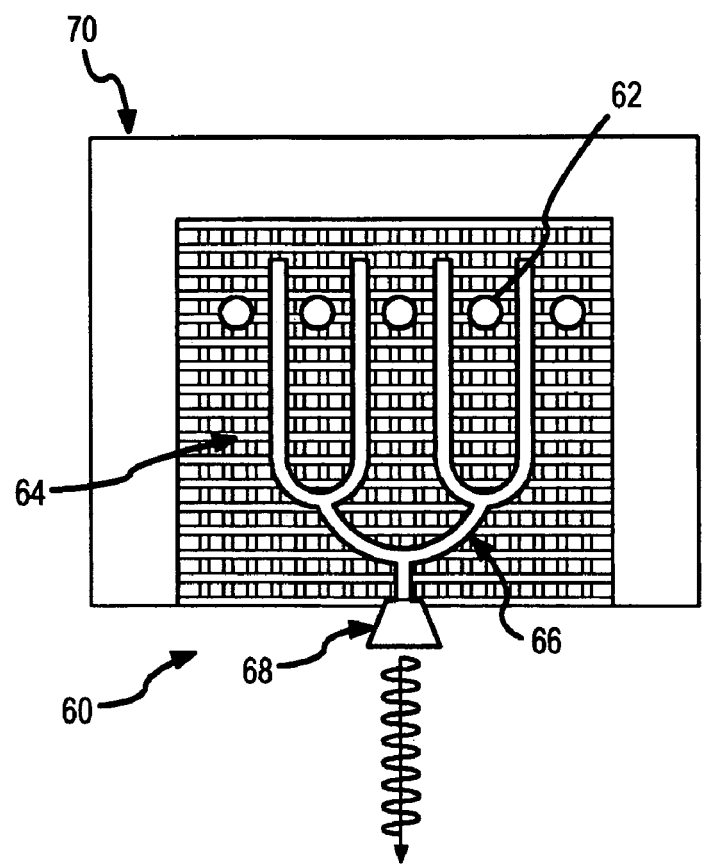
FIG. 6 is a schematic drawing of a THz source with integrated waveguides and defect structures for extracting the radiation.

FIG. 6 is an illustration of a dual-band PC-based THz source 60 that contains both the THz radiation generation and wave guiding functions. A plurality of defect cavities 62 are formed in the coarse structure of a dual-band PC layer 64 to collect and concentrate the THz radiation. Multiple waveguide channels 66 are designed and fabricated in a parallel fashion in the coarse structure of the PC layer to increase power output from a horn antenna 68. In this approach, a network of cavities and waveguides in the coarse structure is used to localize and then couple out thermally powered THz radiation over a large volume of the entire PC structure to one or more micro-machined THz antennas. A thermal source 70 is formed around the exterior of the PC layer. Various architectures and geometries can be implemented using a dual-band PC.

There are two advantages associated with the embedded structures approach. First, the addition of another PC in the overall structure provides more degrees of freedom in designing the photon DOS of the radiation core. One interesting combination would be that the higher-frequency band gap is at the Planck distribution peak so that it strongly suppresses the normal Planck radiation, while the lower-frequency emission peak enhances the THz radiation. Another important advantage of the dual-band PC is that it makes possible the physical integration of the radiation core and a network of radiation collecting and radiation guiding structures. This will lead to further improvement in efficiency and reduction of cost, size and weight of the PC-based THz radiation source.

Figure 7:
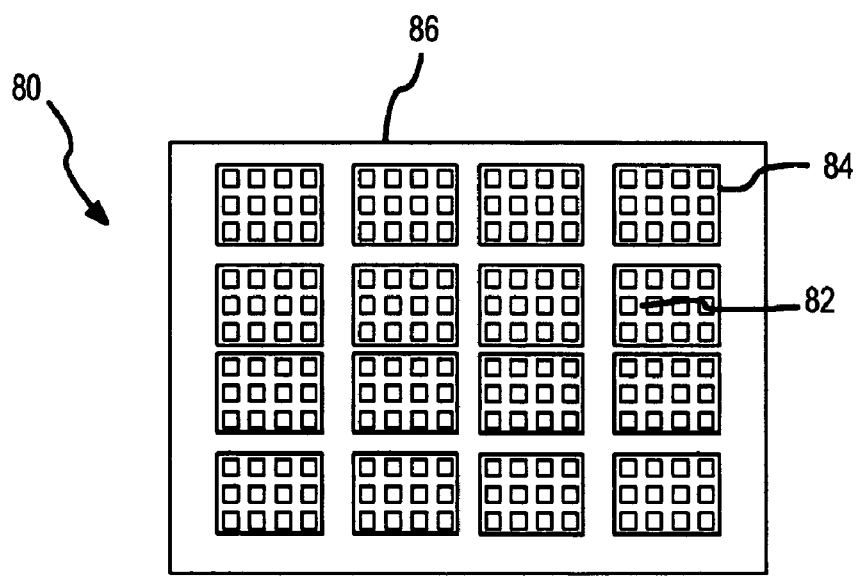
FIG. 7 illustrates a triply-embedded structure for a THz source.

The concept of embedding a fine structure within a coarse structure is not limited to two bands. Periodic structures can be embedded on smaller and smaller scales, determined by the desired effect (band gap or emission peak). In fact, the number of bands is arbitrary and limited only by the ability to design and the capability to fabricate such embedded PCs. A triply-embedded structure 80 is shown in FIG. 7 in which rectangles 82 are embedded within rectangles 84 embedded within rectangle 86. Each rectangle may be comprised of a different material and a matrix may consist of empty space.

First-Order Power Estimation of the PBG-Based Thermally Powered THz Radiation Source The fraction of the total thermal radiation energy included in the THz region of the normal Planck curve is very small, even for high-temperature objects. As the temperature (T) is increased, the fraction of all thermal energy in the THz region decreases as the peak radiation frequency moves further away from the THz region. However, the radiance in the THz band increases almost linearly with T. Therefore an optimal operating T needs to be selected to obtain a high power density while still maintaining reasonable efficiency. Heat must be supplied to the device constantly to compensate for the emission into the THz band. Some quantitative considerations on achievable THz power density are discussed below.

For a normal blackbody object at a temperature T, R(f, T), the Planck energy density as a function of frequency f and T, is described by Eq. (1), $$R(f, T) = \frac{8 \cdot \pi \cdot h \cdot f^3 / c^3}{e^{hf/kT} - 1} \quad (1)$$

Equation (1) has units of Joule/m³/Hz and the Planck constant h=6.63e−34 J s, the Boltzmann constant k=1.38e−23 J /K, the speed of light c=3.0e8 m/s. At a fixed frequency, the temperature dependence is, $$R(T) \propto \frac{1}{e^{hf/kT} - 1} \quad (2)$$

In the THz region, the absolute radiated energy density is almost linear in temperature. Therefore, higher temperature is desired for higher power density. Equation (1) can be written as a product of the photon DOS ρ(f) and the average energy of a thermal photon U(f, T), $$R(f, T) = U(f, T) \cdot \rho(f) \quad (3)$$

Equation (4) is the photon DOS for a normal empty blackbody cavity.

$$DOS = \rho(f) = \frac{4 \cdot f^3}{c^3} \quad (4)$$

so $$U(f, T) = \frac{2 \cdot \pi \cdot h \cdot f}{e^{hf/kT} - 1} \quad (5)$$

From Eqs. (3–5), at a fixed T, the Planck peak $f_{max}$ (maximum emission frequency) can be readily predicted to be a quite broad peak and proportional to T. For example, at T=300 K, $f_{max}$ is at 17.6 THz (17 μm), while for T=1000 K, $f_{max}$ is at 58.7 THz (5 μm). FIG. 1 plots a normal blackbody radiation spectrum 10 for T=1000 K. It is clear that a normal blackbody object is not a useful THz source.

However, for a cavity within a PC, the photon DOS can be engineered to a completely different distribution than Eq. (4). For example, it can be designed to peak at some desired frequency band. FIG. 2 shows a plot of the photon DOS of a particular PC structure that has a completely different distribution (notice the DOS peaks and valleys at the various frequency bands) than Eq. (4).

The new thermal radiation energy density for a cavity in a PC can be calculated by taking the product of the modified photon DOS of the PC and the photon average thermal energy U(f, T). U(f, T) decreases with frequency at any particular temperature T, which is advantageous for THz emission. The frequency dependence of U(f, T) is small. Therefore, the photon DOS will dominate the blackbody radiation spectrum of a cavity in a PC. For a PC cavity, the thermal radiation spectrum can be written as, $$R(f, T) = \left(\frac{2 \cdot \pi \cdot h \cdot f}{e^{hf/kT} - 1}\right) \cdot \rho_{PC}(f) \quad (6)$$

Using Equation (6), with the following assumptions: T=1000 K, f=1.0 THz, from Eq. (5), U(1 THZ,1000K) =8.5e–20 J. Take a PC with a face-centered-cubic lattice of dielectric spheres in air with filling factor=0.3 and refractive index=3.6, periodicity a=330 μm, it leads to $\rho_{pc}$(1.0 THz) =5/m³/Hz. Assuming a bandwidth Δf=0.1 THz, the radiated THz power/unit area=¼*c*U*$\rho_{PBG}$ *Δf=1 mW/cm² (as-suming isotropic radiation).

An alternative way to estimate the photon DOS shift necessary to provide sufficient THz radiation power is given as the following. The total power available from a blackbody cavity=σ*T⁴, where σ=5.67e–8 W/K⁴/m². At T=1000 K, total power density=56700 W/m². By designing a PC with a photon DOS peaked at 1.0 THz and, for example, having bandwidth including 1% of the total DOS, we would be able to increase the power density dramatically around 1.0 THz, power density (1.0 THz)~500 W/m²=50 mW/cm².

While several illustrative embodiments of the invention have been shown and described, numerous variations and alternate embodiments will occur to those skilled in the art. Such variations and alternate embodiments are contemplated, and can be made without departing from the spirit and scope of the invention as defined in the appended claims.

We claim:

1. A thermally powered terahertz (THz) radiation source comprising a photonic crystal (PC) structure that generates a sharp emission peak in the THz region of a modified Planck spectrum using heat as the energy source.

2. The thermally powered THz radiation source of claim 1, wherein the PC has a density of states (DOS) that enhances the emission peak in the THz region.

3. The thermally powered THz radiation source of claim 2, wherein the PC has a DOS that suppresses the emission peak in the infrared (IR) region of the Planck spectrum.

4. The thermally powered THz radiation source of claim 1, wherein the THz region extends from approximately 0.3 to 10 THz.

5. The thermally powered THz radiation source of claim 1, wherein the bandwidth of the emission peak is less than 20% of the center frequency of the peak.

6. The thermally powered THz radiation source of claim 1, wherein the bandwidth of the emission peak is less than 10% of the center frequency of the peak.

7. The thermally powered THz radiation source of claim 1, wherein the emission peak of an unmodified Planck spectrum is shifted from the IR region to the THz region by at least a factor of three in wavelength.

8. The thermally powered THz radiation source of claim 1, further comprising an output antenna that emits the THz radiation.

9. The thermally powered THz radiation source of claim 1, wherein the PC structure is heated above ambient temperature to just below the melting point of the crystal material such that increased output power is produced as needed.

10. The thermally powered THz radiation source of claim 1, further comprising:
   An antenna that emits the THz radiation;
   A waveguide that couples the THz radiation to the antenna; and
   A plurality of defect cavities that concentrate the THz radiation from the PC structure in a limited bandwidth and couple the radiation into the waveguide.

11. The thermally powered THz radiation source of claim 10, wherein the defect cavities and waveguide are integrated with the PC structure.

12. The thermally powered THz radiation source of claim 10, wherein the defect cavities act as narrowband resonators that concentrate the radiation emitted by the PC.

13. The thermally powered THz radiation source of claim 1, wherein the PC structure exhibits a band gap outside the THz region that enhances the emission peak in the THz region.

14. The thermally powered THz radiation source of claim 13, wherein the band gap suppresses thermal emission in the IR region.

15. The thermally powered THz radiation source of claim 13, wherein the PC structure comprises a fine PC structure embedded within a coarse PC structure.

16. The thermally powered THz radiation source of claim 15, further comprising
   An antenna that emits the THz radiation;
   A waveguide that couples the THz radiation to the antenna; and
   A plurality of defect cavities that concentrate the THz radiation from the PC structure and couple it into the waveguide.

17. The thermally powered THz radiation source of claim 16, wherein the waveguide and defect cavities are integrated with said fine and coarse PC structures.

18. A thermally powered THz radiation source, comprising:
   A photonic crystal (PC) core that generates a sharp emission peak in the THz region of a modified Planck spectrum when heated;
   An antenna that emits the THz radiation;
   A waveguide that couples the THz radiation to the antenna; and
   A plurality of defect cavities that concentrate the THz radiation from the PC core in a limited bandwidth and couple it into the waveguide.

19. The thermally powered THz radiation source of claim 18, wherein the defect cavities and waveguide are formed in the PC core.

20. The thermally powered THz radiation source of claim 18, wherein the waveguide and defect cavities are formed in an external PC layer surrounding the PC structure, said layer having a band gap in the THz region to efficiently couple the radiation from the PC structure to the antenna.

21. The thermally powered THz radiation source of claim 18, wherein the defect cavities also act as narrowband resonators that generate a narrowband source.

22. A thermally powered THz radiation source, comprising:
   A coarse photonic crystal (PC) structure that generates an emission peak in the THz region of a modified Planck spectrum when heated; and A fine PC structure embedded in the coarse PC structure that exhibits a band gap outside the THz region that sharpens the emission peak in the THz region.

23. The thermally powered THz radiation source of claim 22, wherein the band gap suppresses thermal emission in the IR region.

24. A thermally powered THz radiation source, comprising:
- A photonic crystal (PC) core that generates a sharp emission peak in the THz region of a photonic crystal modified Planck spectrum when heated, said core comprising a fine PC structure embedded in a coarse PC structure that exhibit respective band gaps that suppress thermal emission in the IR region and enhance thermal emission in the THz region;
- A plurality of defect cavities that collect and concentrate the THz radiation from the PC core;
- A waveguide that combines the collected THz radiation from the defect cavities and directs it to an output port; and
- An antenna at the output port that emits the THz radiation.

25. The thermally powered THz radiation source of claim 24, wherein the defect cavities and waveguide are embedded in the PC core.

* * * * *